(12) United States Patent
Rossiter

(10) Patent No.: US 7,298,473 B2
(45) Date of Patent: Nov. 20, 2007

(54) SPECTROSCOPY CELL

(76) Inventor: Valentine John Rossiter, Old Parish, Dungarvan, Waterford (IE)

( * ) Notice: Subject to any disclaimer, the term of this patent is extended or adjusted under 35 U.S.C. 154(b) by 326 days.

(21) Appl. No.: 11/032,229

(22) Filed: Jan. 11, 2005

(65) Prior Publication Data

US 2005/0168734 A1 Aug. 4, 2005

(30) Foreign Application Priority Data

Jan. 12, 2004 (GB) ................................ 0400567.4

(51) Int. Cl.
*G01N 1/10* (2006.01)
(52) U.S. Cl. ...................... 356/246; 356/244; 356/440
(58) Field of Classification Search ............... 356/244, 356/246, 440; 250/343; 374/55, 56
See application file for complete search history.

(56) References Cited

U.S. PATENT DOCUMENTS 4,420,690 A * 12/1983 Kuehl ......................... 250/428
4,587,835 A 5/1986 Adams
4,674,876 A * 6/1987 Rossiter ...................... 356/244

FOREIGN PATENT DOCUMENTS

GB 2 154 758 A 9/1985

* cited by examiner

*Primary Examiner*—Gregory J. Toatley, Jr.
*Assistant Examiner*—Abdullahi Nur
(74) *Attorney, Agent, or Firm*—Sughrue Mion Pllc.

(57) ABSTRACT

A spectroscopy cell has a body with a central outer sample chamber (6). Within this chamber (6) is a sample cavity (25) as part of a temperature controlled sample probe (23). At one end this sample cavity (25) is delimited by a movable gas connection insert (20) which extends outwardly to a temperature-controlled (e.g. cooled) end plate (8). Gas inlet and outlet tubes (29,30) also extend from the end plate to the sample cavity (25). In use the sample cavity (25) may be at a high temperature so that (a) it is difficult to provide seals for the gas connection insert (20) and gas tubes (29,30); and (b) they are subject to considerable thermal expansion and contraction. Similar problems occur with very low cavity temperatures. Therefore compressible seals (21,31,32) are provided in the end plate (8), remote from the chamber.

21 Claims, 5 Drawing Sheets

SPECTROSCOPY CELL

BACKGROUND OF THE INVENTION

The present invention relates to a spectroscopy cell. It particularly relates to a method and means suitable for providing a low volume flow-through cell for spectroscopy, especially for samples at extreme temperatures.

There is a requirement to provide a spectroscopy cell to examine such processes as gas-solid interactions, often required in the field of catalyst research and other research areas. In some such studies the flow of a gas across a solid material must be controlled so that the gas volume is low and so that the flow path is exposed to the optical beam of the spectrometer, often arranged so that the beam interacts with the region of the solid first contacted by the gas. Such arrangements are necessary to enable meaningful time based studies of the gas-solid interaction as a function of temperature and other experimental parameters. A preferred embodiment of this invention provides a method by which the maximum temperature can be substantially increased over methods previously developed and providing much lower volumes than available from methods previously developed while meeting the requirements for a well defined gas flow path. The invention is not restricted to a particular optical range or to a particular optical technique or to a particular sample format or to a specific sample material or gas or fluid.

Rossiter (U.S. Pat. No. 4,674,876) has shown how very high sample temperatures can be achieved in a gas environment with spectroscopic access. But that invention does not address the problem of providing a very low gas volume (less than 10 ml) around the sample region. There are a number of difficulties in defining a low gas volume in the region of a sample to which there is to be optical access and around which a well defined gas flow path must be maintained. The difficulties are compounded by differential thermal expansion and the requirement to maintain gas connections as the temperature of the sample is varied. At the temperatures addressed here (in excess of 300 deg C. or below 0 deg C.), where conventional sealing methods (such as polymeric o-rings) cannot be used in contact with the sample region, yet it is necessary to provide gas connections and define a flow path in this region of high or low temperature.

SUMMARY OF THE INVENTION

In a first aspect the invention provides a spectroscopy cell comprising a body within which is defined a sample cavity; one or more elongate elements each of which extends from a first region at or adjacent the cavity to a respective second region remote from the cavity; and respective compressible seal means at the second region for sealing to the elongate element to accommodate thermal expansion and contraction.

In a second aspect the invention provides a method of maintaining gas connections between a low volume spectroscopic sample cavity and gas transport tubes when there is a substantial temperature differential between the cavity and the exterior such that during thermal expansion and contraction this connection is maintained by the spring-like properties of compressed o-rings or other soft seals remotely located from the sample cavity in a controlled temperature region.

In a third aspect the invention provides a method of sealing an open access sample region in a low volume, spectroscopic sample cavity when there is a substantial temperature differential between the cavity and the exterior such that during thermal expansion and contraction sealing is maintained by face-to-face contact between the end face of the sample enclosure and a movable piece which is supported by the spring-like action of o-rings or other soft seals remotely located from the sample cavity in a controlled temperature region.

An embodiment of the invention will now be described with reference to the accompanying drawings. This particular embodiment is suitable for high temperature operations.

DETAILED DESCRIPTION OF THE INVENTION

Figure 1A:
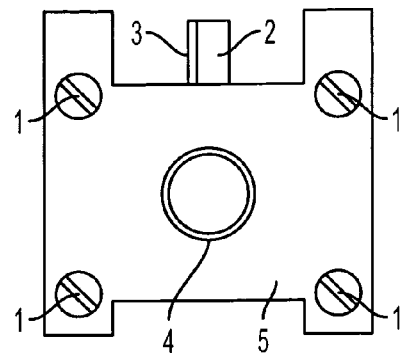
FIG. 1(a) is an end view of a spectroscopy cell of the present invention.
Figure 1B:
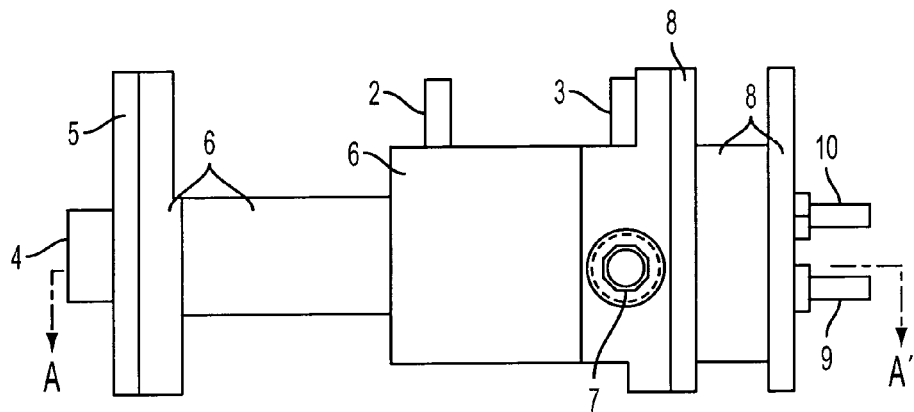
FIG. 1(b) is a side view thereof.
Figure 1C:
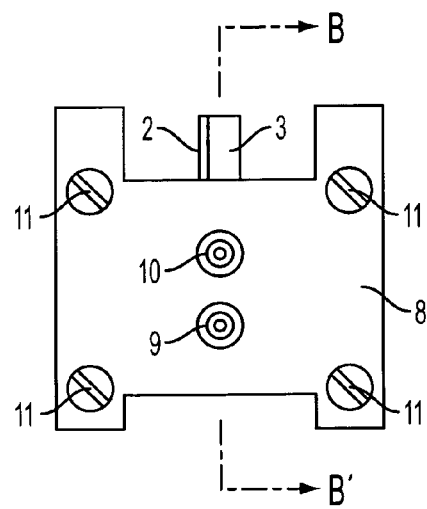
FIG. 1(c) is an opposite end view thereof.
Figure 2:
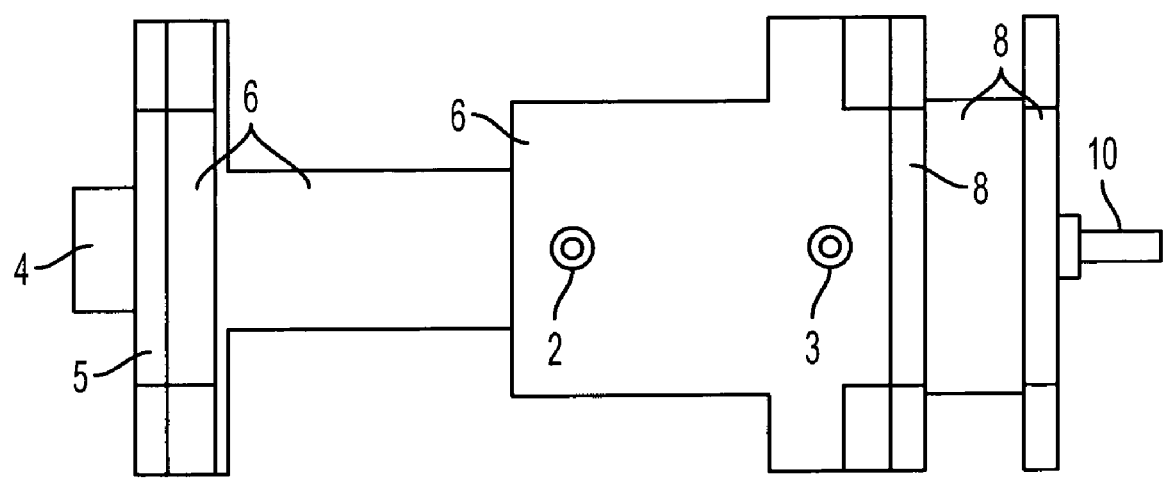
FIG. 2 is a top view thereof.

FIGS. 1(a)-1(c) illustrate the external form of this embodiment where appropriate external cooling can be added using conventional means. A central chamber (6) can be formed in a material such as stainless steel with optical access window port screw (7) on one side of the chamber (corresponding to a second such window port on the opposite side of the chamber). A drilled through pipe access (2) allows insertion of a location key into the chamber while drilled through pipe access (3) allows insertion of a thermocouple by which the local sample temperature in the chamber can be monitored. The chamber is fitted with two end plates. End Plate (5) carries the sample mounting which is electrically heated with electrical leads passing through port (4) formed in the end plate (5) which is secured to the chamber (6) by screws (1). End Plate (8) is secured to the chamber (6) by screws (11) and carries gas inlet port (9) and outlet port (10). FIG. 2 shows a top view of the chamber (6) and the end plates (5) and (8).

Figure 3:
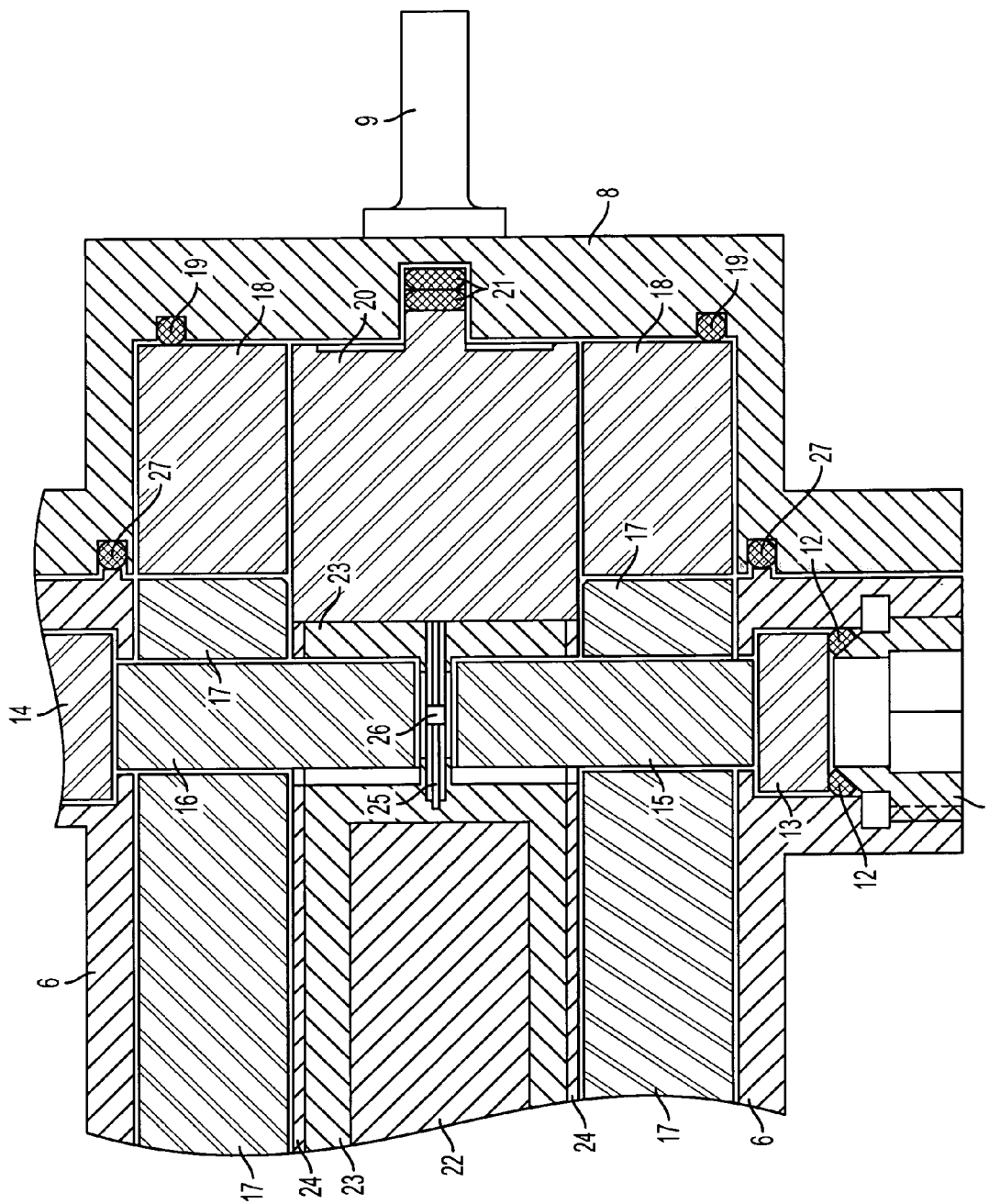
FIG. 3 is a section view taken along section A-A' of FIG. 1(b)

FIG. 3 shows a partial view of cross-section A-A' providing one view of the internal structure of the assembly. The chamber is sealed at the optical access ports by screw (7), o-ring (12) and window (13). This is replicated on the opposite side of the chamber for window (14). The region from the external windows (13 and 14) towards the sample location slot (25) is occupied by window blanks (15) and (16) which maintain optical access while removing dead volume. Note that other embodiments of the invention could use fiber optic probes as an alternative means of optical access. Structure (17) is formed in a low thermal conductivity material (such as a ceramic) and surrounds the sample probe (23) to reduce dead volume. The sample probe (23) contains an electrical heating element (22) and may be fitted with a sleeve (24). Slot (25) locates the sample (generally a thin disc shaped or rectangular sample) and allows gas access through (26) where the gas can flow on each side of the sample in the sample slot. Access to one end of the sample slot (25) is closed by the face of the movable gas connection insert (20) which can be formed in a low thermal conductivity material (for example, a ceramic). Item (20) can slide within (18) and as the temperature of the sample probe (23) increases and causes thermal expansion, item (20) is pushed back against a remote compressive element (21) which can conveniently be formed by using o-rings. Note that these o-rings reside in end plate (8) which is cooled. End Plate (8) is sealed to chamber (6) by o-ring (27). Item (18) again serves to reduce dead volume and house (20) and is supported by o-ring (19) which allows for differential thermal expansion within the entire assembly.

Figure 4:
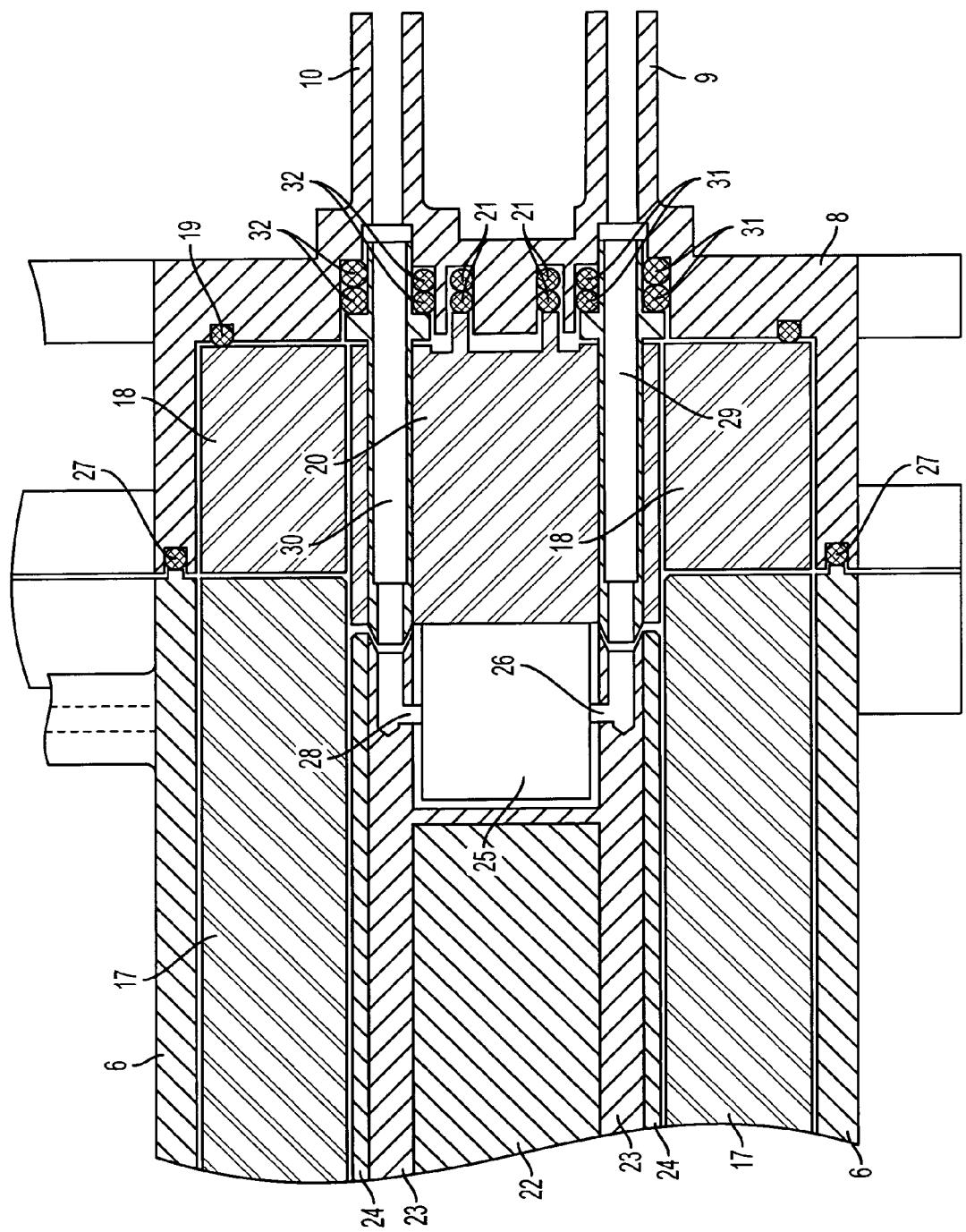
FIG. 4 is a sectional view taken along section B-B' of FIG. 1(c)

FIG. 4 shows a partial view of cross-section B-B'. This view illustrates the method employed to maintain the gas connection to the sample cavity (25) as the sample probe moves with increasing temperature. This view of the sample location cavity (25) shows the gas inlet point (26) and gas outlet point (28) formed in the sample probe (23). The movable gas connection insert (20) carries movable gas inlet tube (29) which is supported by remote compressive o-rings (31) and movable gas outlet tube (30) which is supported by remote compressive o-rings (32). These remote o-rings (31 and 32) are housed in cooled end plate (8) and exert a force on the gas tubes (29 and 30) so that they maintain surface to surface contact with the corresponding faces formed in sample probe (23). The particular form of this surface to surface contact shown here (tapering faces) is only one of a number of forms that can be used to provide a suitable seal. Others include plane face to face contact with the possible addition of a metal disc. It will also be appreciated that in other embodiments the same effect may be obtained without the use of separate movable tubes (29 and 30) by forming the coupling in item (20) as this too is force loaded by o-rings (21).

Figure 5A:
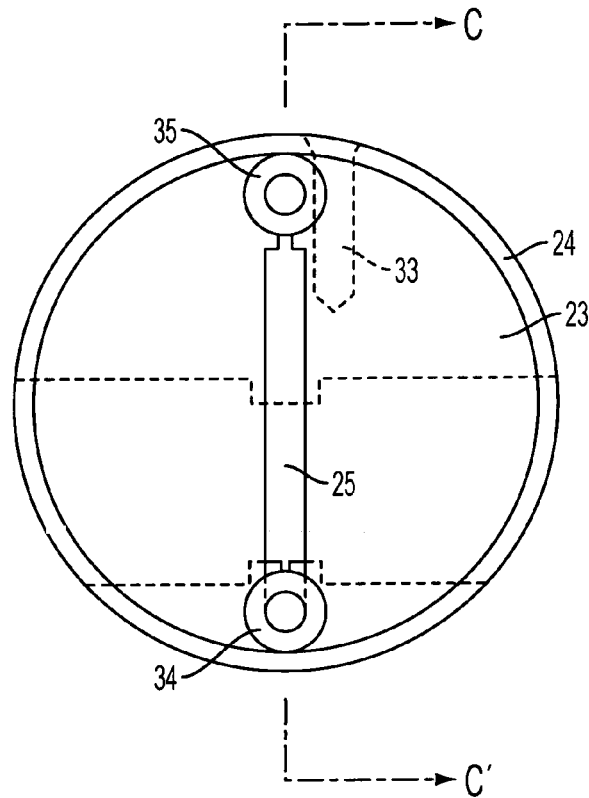
FIG. 5(a) is an end view of the sample probe according to the present invention.
Figure 5B:
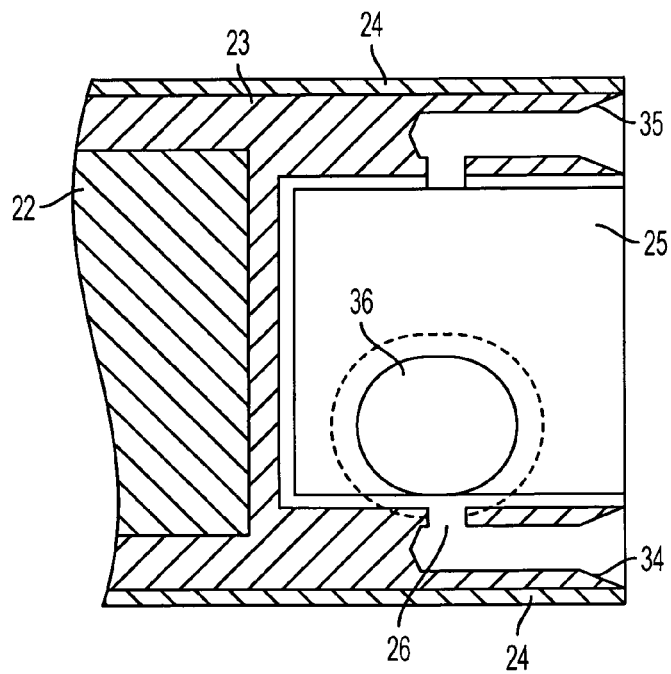
FIG. 5(b) is a sectional view thereof taken along section C-C' of FIG. 5(a).

FIGS. 5(a) and 5(b) show the end face of the sample probe (23) and partial cross-section C-C'. The location cavity (33) is for the insertion of a read-out thermocouple via (3) in chamber (6). The profile of the gas inlet sealing face is shown (34) and the profile for the gas outlet sealing face is shown (35). The optical apertures (36) in the sample probe (23) may be slightly elongated to allow for the thermal expansion of the sample probe as its temperature is increased. Note that the optical apertures (36) are aligned close to the gas inlet (26) so that the initial reaction between gas and sample can be observed.

The invention does not inherently limit the upper temperature which is determined by choice of materials and relative dimensions.

The invention is also applicable to low temperature sample environments where the compressive soft-seal components would be in a temperature regulated environment to maintain their spring-like characteristics, typically by maintaining them at near ambient temperatures.

The invention allows the maintenance of the gas flow path over a wide range of operational pressures from vacuum to high pressure.

The invention is not restricted to the particulars of the illustrative embodiment described here.

What is claimed is:

1. A spectroscopy cell comprising:
   external wall portions defining a chamber including an end wall portion;
   a sample probe located within said chamber, spaced from said end wall portion, said probe defining a sample slot for holding a sample;
   a first temperature control device for controlling the temperature of a sample slot;
   a second temperature control device in thermal contact with the chamber end wall portion for controlling the temperature thereof;
   an elongate element adjacent the sample probe and disposed between the sample probe and the chamber end wall portion, said elongate element being moveable upon expansion and contraction of the sample probe due to temperature change; and
   a compressible member located between the elongate element and the chamber end wall portion for absorbing the movement of the elongate element toward and away from the end wall portion, whereby the elongate element and the sample probe remain adjacent each other.

2. A cell according to claim 1 wherein said elongate element has fluid flow conduits for conducting fluids between the exterior of the cell and the sample slot.

3. A cell according to claim 1 wherein the elongate element is in surface to surface direct contact with the sample probe.

4. A cell according to claim 1 wherein the compressible member permits relative displacements of at least 1 mm.

5. A cell according to claim 1 wherein the sample probe has an aligned pair of optical apertures confronting each other across the sample slot for the passage of radiation for investigating a sample in the sample slot.

6. A cell according to claim 5 having a first fluid flow conduit for conveying a fluid to the sample slot and a second fluid flow conduit for conveying a fluid away from the sample slot; and wherein the first fluid flow conduit opens into the slot adjacent the line of alignment of the optical apertures.

7. A cell according to claim 1 wherein the chamber contains volume filling elements for reducing the internal fluid volume of the cell.

8. A cell according to claim 7 wherein the internal fluid volume of the cell is below 10 ml.

9. A cell according to claim 1 adapted to operate with a sample cavity at a temperature exceeding 300° C.

10. A cell according to claim 1 adapted to operate with a sample cavity at a temperature exceeding 350° C.

11. A cell according to claim 1 adapted to operate with a sample cavity at a temperature of 350°-600° C.

12. A cell according to claim 1 adapted to operate with a sample cavity at a temperature below 0° C. by heating the end walls to maintain a local temperature above 0° C. in said walls.

13. A cell according to claim 1 which is adapted to be operated at pressures at least as high as 1000 psi or at pressures of at least as low as $10^{-3}$ torr.

14. A cell according to claim 1, wherein said compressible member is an O-ring.

15. A cell according to claim 1, wherein said compressible member includes a plurality of O-rings.

16. A cell according to claim 1, where the elongate element is in direct contact with the compressible member.

17. A spectroscopy cell comprising:
   a housing including an end wall portion and defining a chamber therein, said housing being cooled externally or heated externally;
   a sample probe located within said chamber and spaced from said end wall portion, said probe having a sample slot for holding a sample;
   a temperature control device for controlling the temperature of the sample slot; and
   a moveable element adjacent the sample probe and disposed between the sample probe and the chamber end wall portion, said moveable element being moveable upon expansion and contraction of the sample probe due to temperature change, said moveable element having a first conduit for supplying fluid to the sample slot and a second conduit for removing fluid from the sample slot.

18. The cell of claim 17, further comprising a compressible member located between the moveable element and the chamber end wall portion for absorbing the movement of the moveable element toward and away from the end wall portion.

19. The cell of claim 17, wherein said first and second conduits extend through said end wall portion.

20. The cell of claim 19, further comprising means for retaining said conduits to said end wall portion.

21. The cell of claim 20, wherein said retaining means includes an O-ring.

* * * * *